United States Patent [19]
Inagaki et al.

[11] Patent Number: 5,687,732
[45] Date of Patent: Nov. 18, 1997

[54] BLOOD PRESSURE MONITOR

[75] Inventors: Takashi Inagaki; Toshiyuki Kobayashi, both of Kyoto, Japan

[73] Assignee: Omron Corporation, Kyoto, Japan

[21] Appl. No.: 539,911

[22] Filed: Oct. 6, 1995

[30] Foreign Application Priority Data

Oct. 7, 1994 [JP] Japan ................................ 6-243926
Jan. 18, 1995 [JP] Japan ................................ 7-005716

[51] Int. Cl.⁶ ...................................................... A61B 5/02
[52] U.S. Cl. ............................ 128/672; 128/690; 128/677; D14/100
[58] Field of Search ........................... 128/672, 688, 128/689, 690, 677; D10/132; D14/100, 106

[56] References Cited

U.S. PATENT DOCUMENTS

| 4,195,642 | 4/1980 | Price et al. | 128/689 |
| 5,243,549 | 9/1993 | Oshiba | D14/106 |

FOREIGN PATENT DOCUMENTS

| 2 561 938 | 4/1985 | France. | |
| 680 34 086.9 | 9/1981 | Germany. | |
| 234143 | 2/1990 | Japan | A61B 5/022 |
| 616 801 G | 4/1980 | Switzerland. | |

*Primary Examiner*—Lee S. Cohen
*Assistant Examiner*—Rasiland Kearney
*Attorney, Agent, or Firm*—Morrison & Foerster LLP

[57] ABSTRACT

A blood pressure monitor includes a main body provided with a power switch and an inflating switch, a cover mounted on the main body in an open-and-close fashion and on an inner wall thereof provided with a display, and a cuff secured to the main body as a single unit. When the cover is closed during not using the monitor, the power and inflating switches are covered with the cover. When the cover is opened for use, the display appears. Thus, the blood pressure monitor provides avoidance of unexpected actuation of the power and inflating switches, improvement of operation of the switches and a view angle of the display, improved assembling work of the monitor, and simplification of repair and replacement in the monitor.

6 Claims, 13 Drawing Sheets

(a)

(b)

(a)

(b)

(a)

(b)

BLOOD PRESSURE MONITOR

BACKGROUND OF THE INVENTION

1. Field of the Invention

This invention is in the field of blood pressure monitors such as wrist-type or arm-type blood pressure monitors.

2. Discussion of the Related Art

There is well known a wrist-type blood pressure monitor of FIG. 13 which is disclosed in the Japanese patent laid-open publication No. Hei 2-34143. The monitor includes a main body 220 which is provided With a power switch 221 for turning on or off a power supply, an inflating switch 222 for inflating a cuff and a display 223 employing a LCD, and a cuff 225 attached to the main body 220 as a single unit to be mounted on an operator's wrist.

The conventional blood pressure monitor, however, has the disadvantages that the power switch or the inflating switch is liable to be unexpectedly actuated to waste a source battery when the monitor is carried in a bag and the display is hard to be watched because it is small and secured to the main body. If an operator using the monitor wants to watch the display during measurement, the operator's good posture for measuring has to be deformed resulting in wrong measurement.

When a cuff is necessary to be removed from a main body of a conventional blood pressure monitor for maintenance, inspection, repair or component replacement, such removal is not easy and consumes time.

SUMMARY OF THE INVENTION

It is, therefore, a primary object of this invention to provide a blood pressure monitor for protecting an operation switch, such as power and inflating switches, of the monitor from any unexpected actuation.

It is another object of this invention to provide a blood pressure monitor employing a large scale display for an improved view so positioned that an operator can watch measured values on the display without deforming the operator's good posture during the blood pressure measurement.

It is still another object of this invention to provide a blood pressure monitor employing a cuff which may be easily attached to and removed from a main body.

According to a first aspect of this invention, there is provided a blood pressure monitor which includes a cover disposed on a main body in an open-and-close fashion, a display disposed on the cover opposite to an operation switch for displaying measured data, the operation switch being designed to be covered by the cover when the cover is closed. When the blood pressure monitor is not used, the cover is closed to cover the operation switch without exposing the same to the external from the main body, so that the operation switch is prevented from unexpectedly actuated when the monitor is carried. The display is so disposed on the cover that the cover and the operation switch are separately disposed with enlarged space respectively and the display provides improved sight. Moreover, as the operation switch is composed of a power switch and an inflating switch, power supply or start of inflating can be avoided during carriage.

According to a second aspect of this invention, there is provided a blood pressure monitor in which a cover carrying a display is retained by a main body at a desired angle between 0 and 180 degrees. The cover can be retained in a position of the main body for good sight of the display, whereby the display of measured values can be seen by an operator without deforming the operator's correct posture during measurement.

According to a third aspect of this invention, there is provided a blood pressure monitor in which a cover is engaged with a main body at a predetermined angle of inclination, whereby a display can be seen in an improved position by an operator and the measurement can be made in an operator's natural posture.

According to a fourth aspect of this invention, there is provided a blood pressure monitor in which a cover is mounted on a main body through a hinge piece disposed on a housing of the main body in an open-and-close fashion, so that assembling the blood pressure monitor is improved and components (particularly, display) are easily repaired or replaced.

According to a fifth aspect of this invention, there is provided a blood pressure monitor which includes a main body having a housing provided with a battery storage chamber and an attachment means disposed in the battery storage chamber for attaching a cuff to the main body. Upon operation of the attachment means after opening the battery storage chamber which is easily opened or closed, a cuff is easily attached to or detached from the housing of the main body to thereby provide easy attachment and detachment of the cuff.

BRIEF DESCRIPTION OF THE DRAWINGS

Other objectives and advantages of this invention will be more readily apparent from the following detailed description provided in conjunction with the following figures, of which.

DETAILED DESCRIPTION OF THE INVENTION

Figure 1:
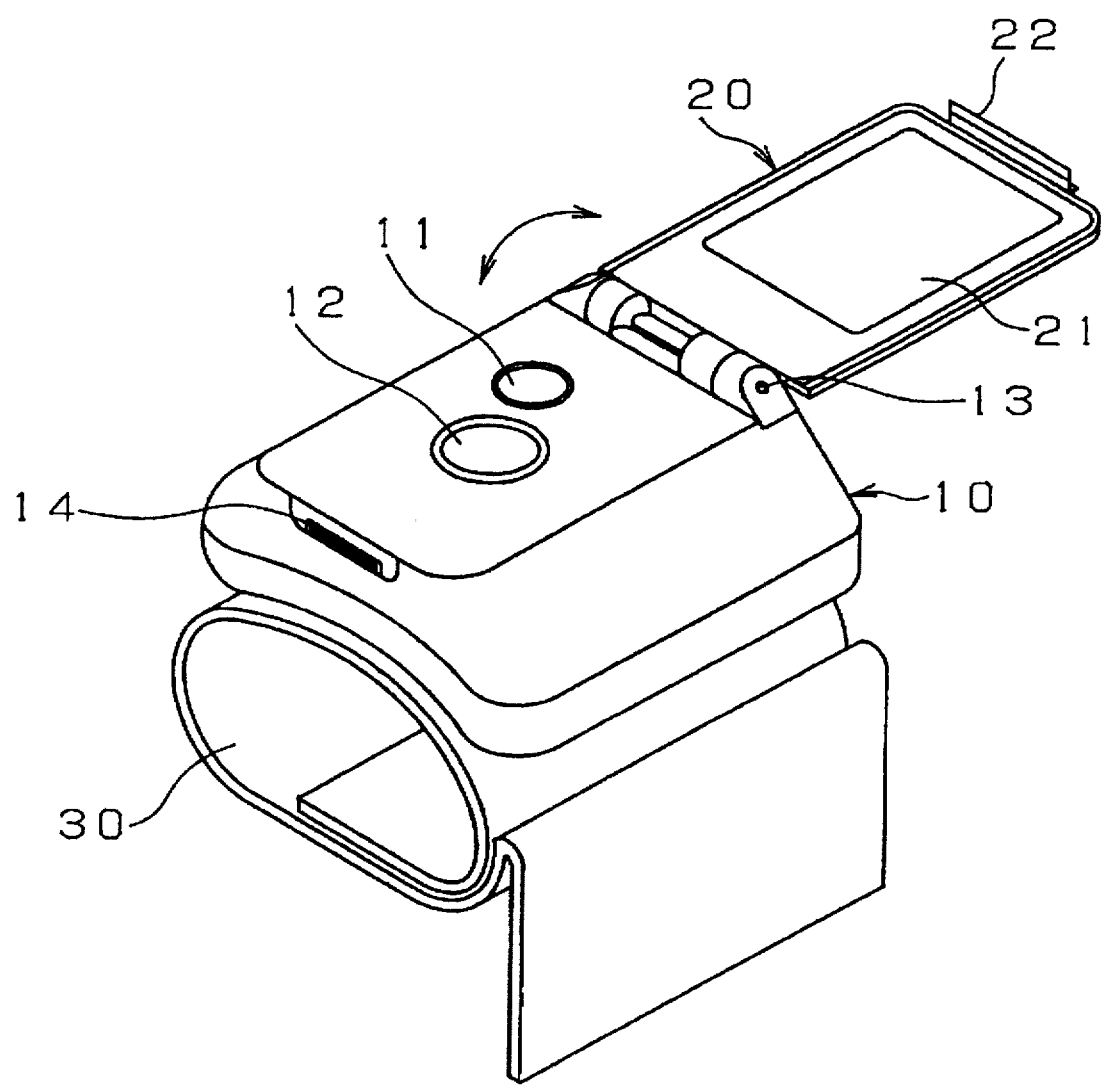
FIG. 1 is a perspective external view of a wrist-type blood pressure monitor as a preferred embodiment of this invention.
Figure 2:
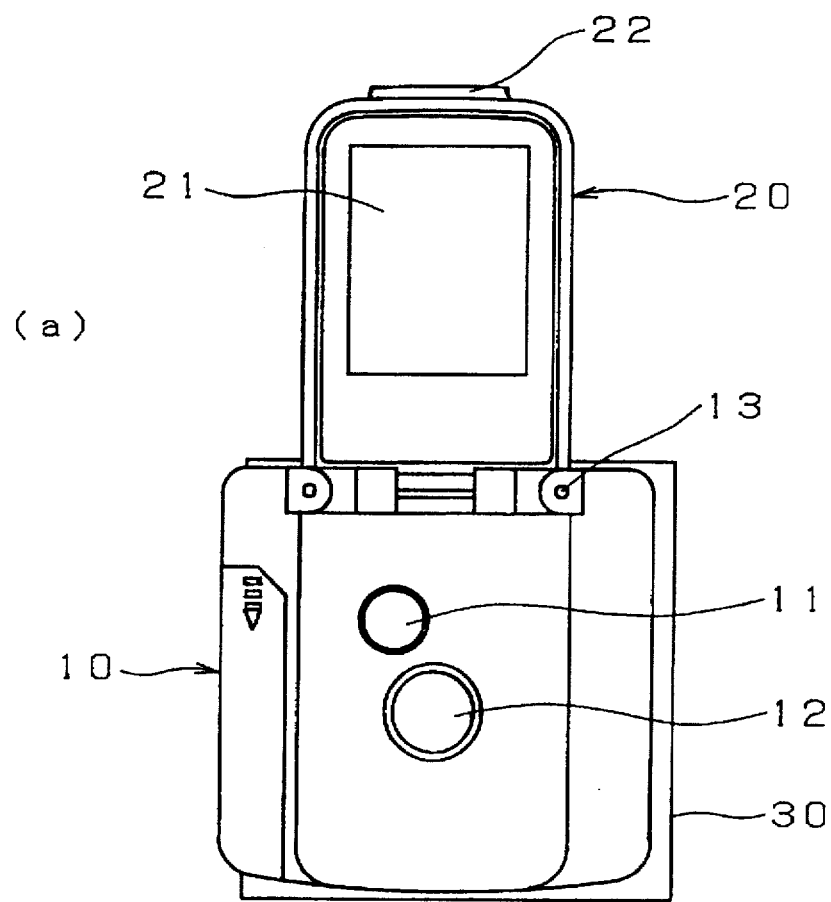
FIG. 2 shows at (a) a plane view of the wrist-type blood pressure monitor of FIG. 1 in which a cover is opened and at (b) a plane view of the monitor in which the cover is closed.
Figure 2:
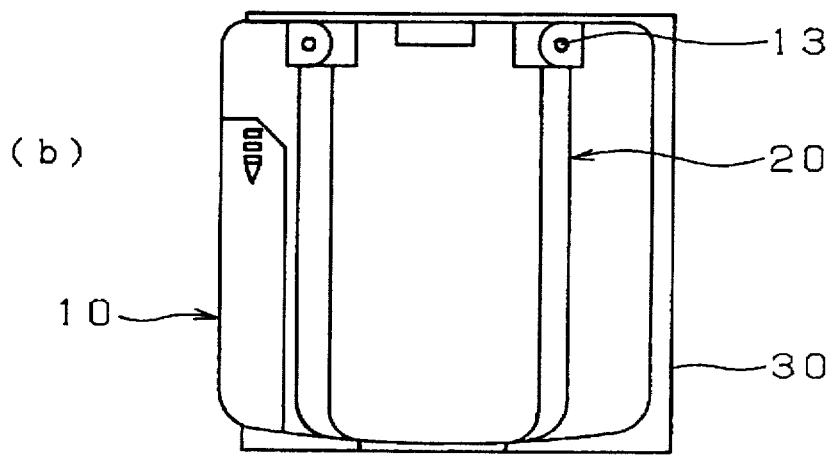

Referring, now, to FIG. 1, there is shown a perspective view of a wrist-type blood pressure monitor as a preferred embodiment of this invention. FIG. 2 shows at (a) a plane view of the wrist-type blood pressure monitor of FIG. 1 in which a cover is fully opened and at (b) a plane view of the monitor in which the cover is completely closed. The blood pressure monitor includes a main body 10 provided with a power switch 11 and an inflating switch 12 as an operation switch, a cover 20 on an inner wall provided with a display (LCD) 21 mounted on the main body in an open-and-close fashion to display blood pressure values, and a cuff 30 secured to the main body 10 in a fixed position as a single unit. The cover 20 is hinged on the main body 10 through a shaft 13 pivotally disposed in a connecting portion to be opened and closed, and may be locked in a close position by engagement between a projection 22 formed on an opposite end of the cover to the connecting portion and a groove 14 formed on the main body 10 corresponding to the projection. The operation switch includes the power switch 11 for turning on and off the power supply and the inflating switch 12 for inflating the cuff 30.

As shown in FIG. 1, since the LCD 21 is disposed on the inner wall of the cover 20, on an upper wall of the main body 10 there are disposed only power and inflating switches 11 and 12, whereby the LCD 21 may be designed to have a large scale corresponding to a space of the cover 20 and the switches 11 and 12 also may be designed to have large buttons to improve the operation. The LCD 21 therefore confronts the operation switches 11 and 12 for displaying measured data. Since the cover 20 is closed during carriage, the switches 11 and 12 are prevented from unexpected actuation to avoid wasted consumption of a source battery and inflation of the cuff 30 unmounted.

Figure 3:
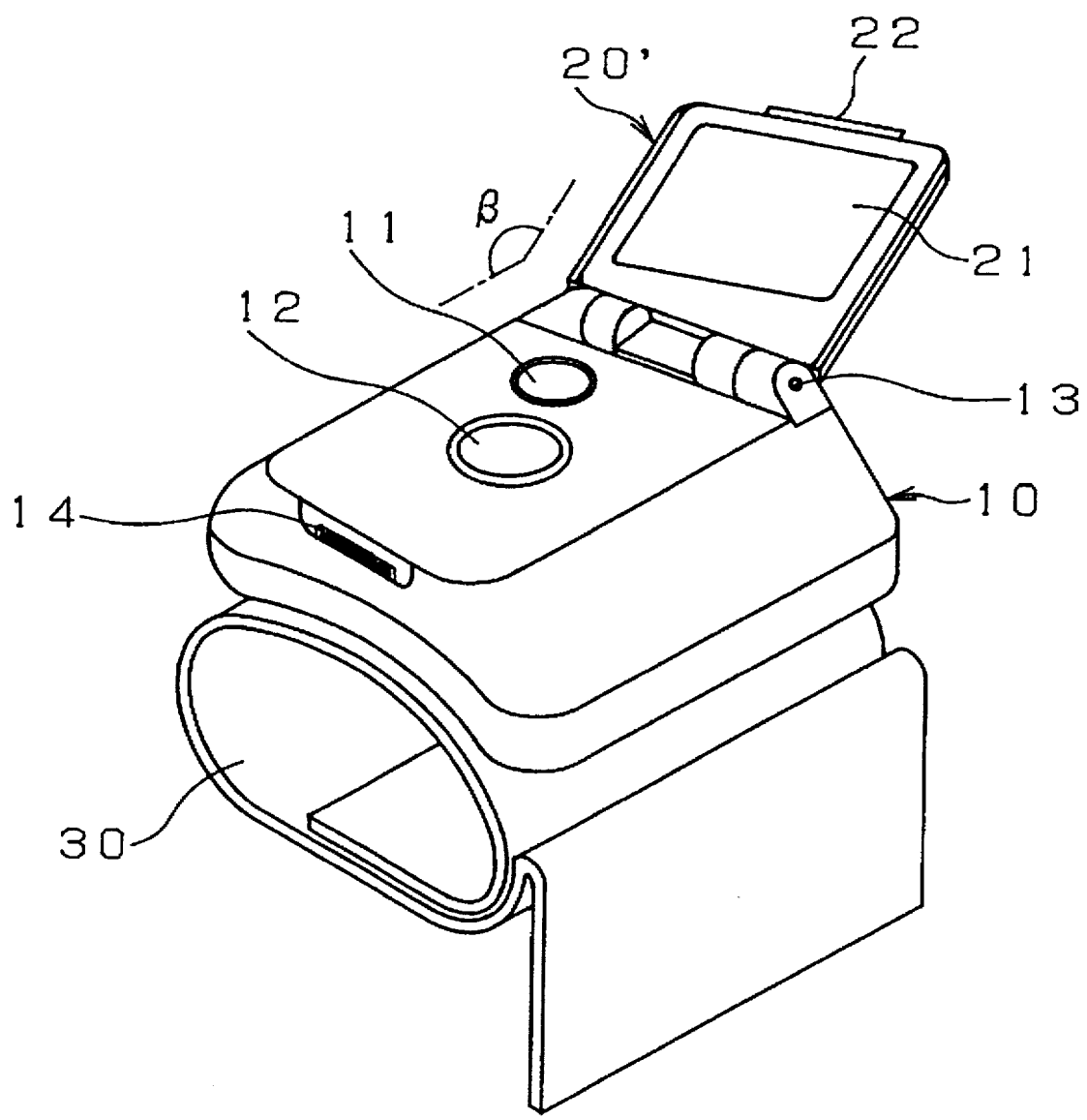
FIG. 3 is a perspective external view of a wrist-type blood pressure monitor as a modification of the monitor of FIG. 1.
Figure 4:
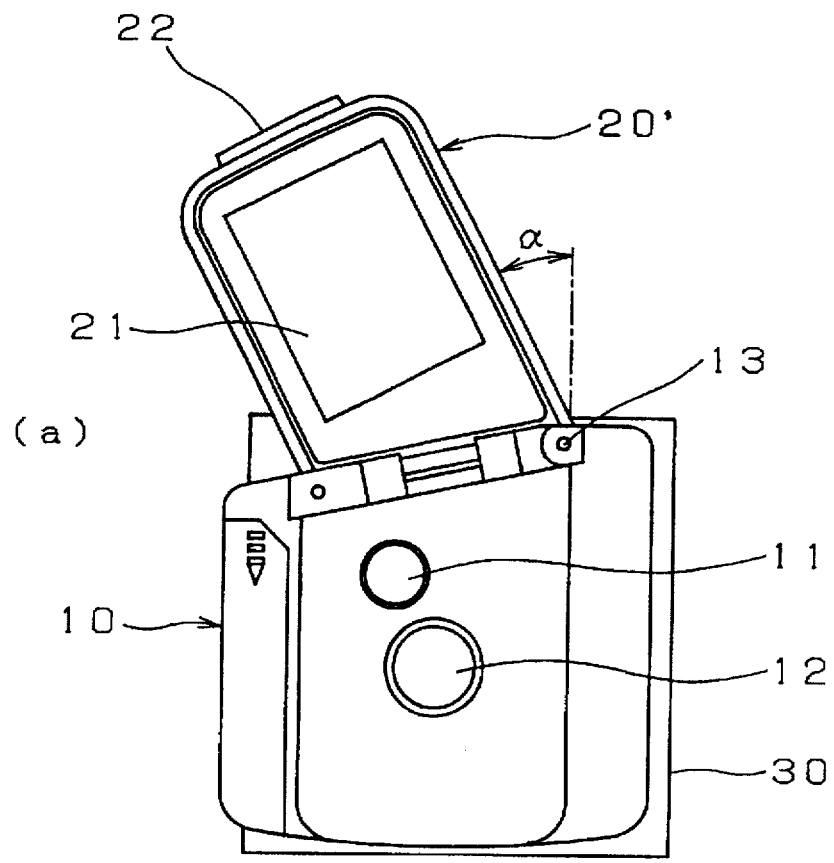
FIG. 4 shows at (a) a plane view of the wrist-type blood pressure monitor of FIG. 3 in which a cover is opened and at (b) a plane view of the monitor in which the cover is closed.
Figure 4:
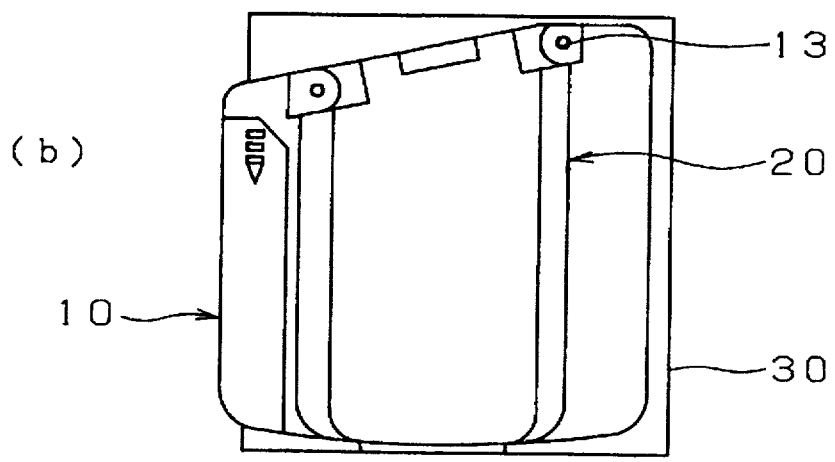
Figure 5:
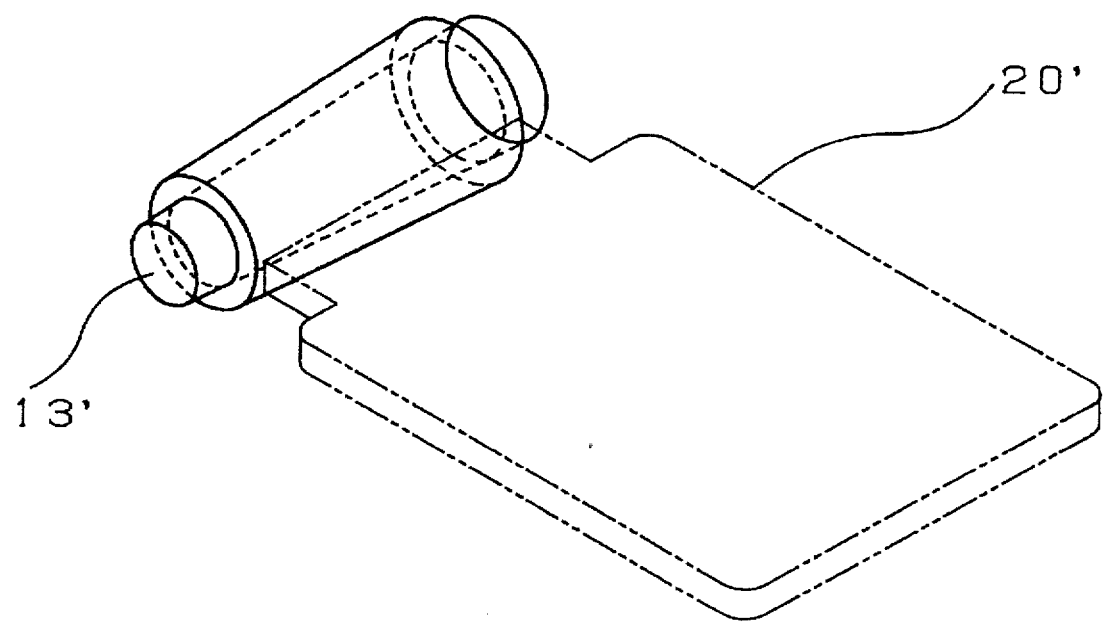
FIG. 5 is a modification of the monitor of FIG. 3 in which a shaft connecting the cover with a main body is modified.

In FIG. 3, there is shown a perspective external view of a wrist-type blood pressure monitor as a modification of the monitor of FIG. 1. FIG. 4 shows at (a) a plane view of the monitor in which a cover is opened, and at (b) a plane view of the monitor in which the cover is closed. This monitor substantially has a same construction as that of the monitor of FIG. 1, but a cover 20' makes a predetermined angle of inclination to the main body 10. The cover 20' is supported in an open-and-close fashion by shaft 13 pivotally mounted at an inclination angle on one end of main body 10 connected with the cover, and has a slant end near the shaft 13. The shaft 13 retains the cover 20' at a predetermined angle as the cover 20' is opened. Accordingly, as the cover 20' is opened, it stands in an inclined position as shown in FIG. 4 (a). Therefore, the shaft 13 is inclined with respect to an opposite end of the main body 10 to one end thereof and an opposite end of the cover 20' to the one end thereof so that the main body 10 and the cover 20' make a predetermined angle of inclination. Alternately, the shaft 13 itself may be modified to have a conical configuration to support the cover 20' at an inclination angle as shown in FIG. 5.

It is recommended that an inclination angle α of the LCD 21 disposed on the inner wall of the cover 20' inclining to the main body 10 (a central axis direction of an operator's arm) is between 20° and 30°, preferably 25°, and an open-and-close angle β of the LCD 21 (FIG. 3) to an upper wall (to be covered by the cover 20') of the main body 10 is between 0° and 180°. As the inclination angle α is designed to be between 20° and 30° though 25° is the best, an operator can easily identify characters and figures displayed on LCD 21 in a relaxed posture when the operator mounts the cuff 30 on a wrist of the operator for blood pressure measurement. As the inclination angle α is designed to be less than 20° or larger than 30°, the display of the LCD 21 is hard to be watched and the arm of the operator has to be moved to find better display resulting causing unnatural force applied to the operator's measuring posture resulting in fluctuation of measured data. Though the open-and-close angle β may be designed to be between 0° (completely closed) and 180° (completely opened), 170° is the best angle to provide the best view of LCD 21 when the angle made by a visual line of an operator in a relaxed posture and a view line of the LCD is considered. If the maximum open angle is designed to be smaller or larger than 170°, the view of characters and figures on the LCD 21 is reduced. Thus, by designing the angles α and β for the best angles in view of human engineering, measurement can be performed in a natural posture of the operator and the best view is provided by the LCD 21.

Figure 6:
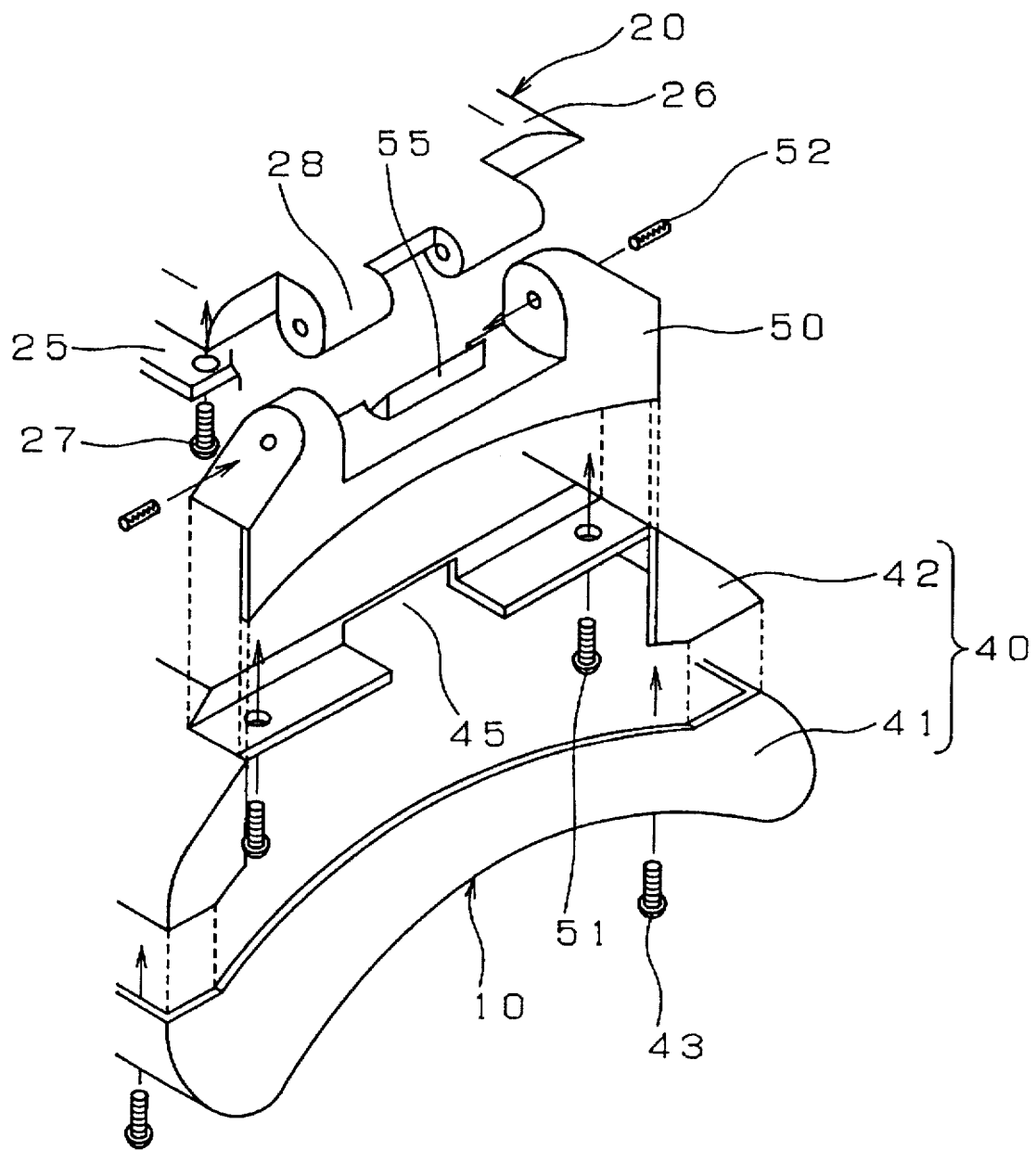
FIG. 6 is a disassembled view showing a modified construction of a connection unit of the cover and the main body in the blood pressure monitor.

Though the covers 20 and 20' are supported by the shafts 13 and 13' pivotally mounted on the main body 10 in the foregoing embodiments, FIG. 6 is a perspective disassembled view showing a modified connection unit of a cover and a main body. A main housing 40 of main body 10 includes an external large housing 41 and an internal small housing 42 which are jointed together by screws 43 as a single unit. At one end of the small housing 42 there is disposed a hinge piece 50 which is secured to the housing 42 by screws 51 for mounting the cover 20 thereon. A shaft portion 28 of cover 20 in which a front panel 25 is secured to a base panel 26 by screws 27 is pivoted at a predetermined position of the hinge piece 50 by spring pins 52 for opening-and-closing the cover 20.

Figure 7:
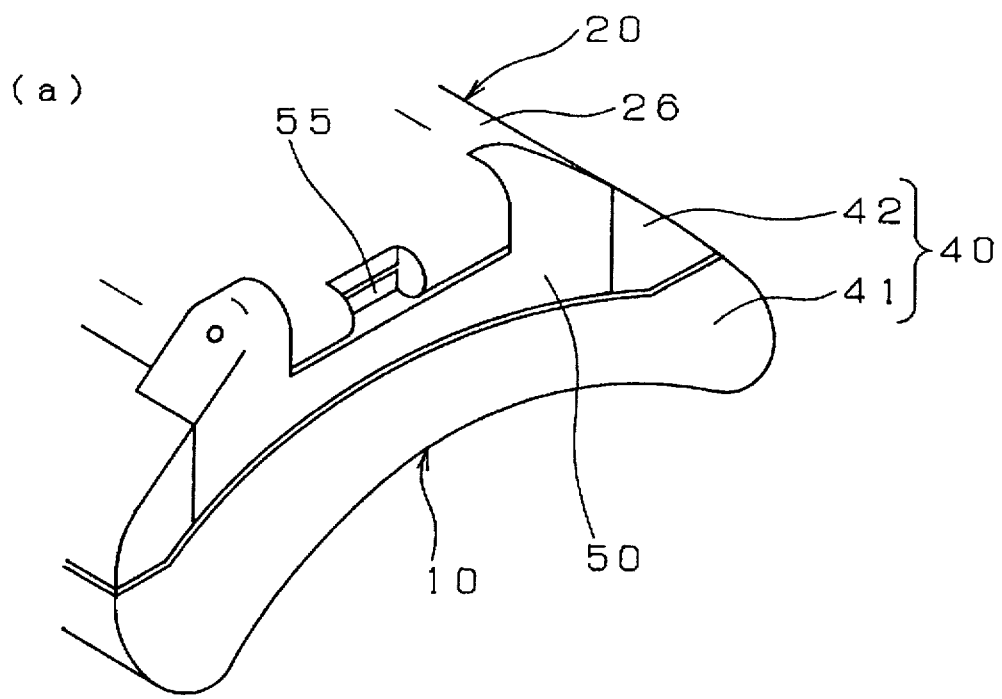
FIG. 7 shows at (a) a partial perspective view of the connection unit of FIG. 6 in which a cover is closed and at (b) a partial perspective view of the monitor in which the cover is opened.
Figure 7:
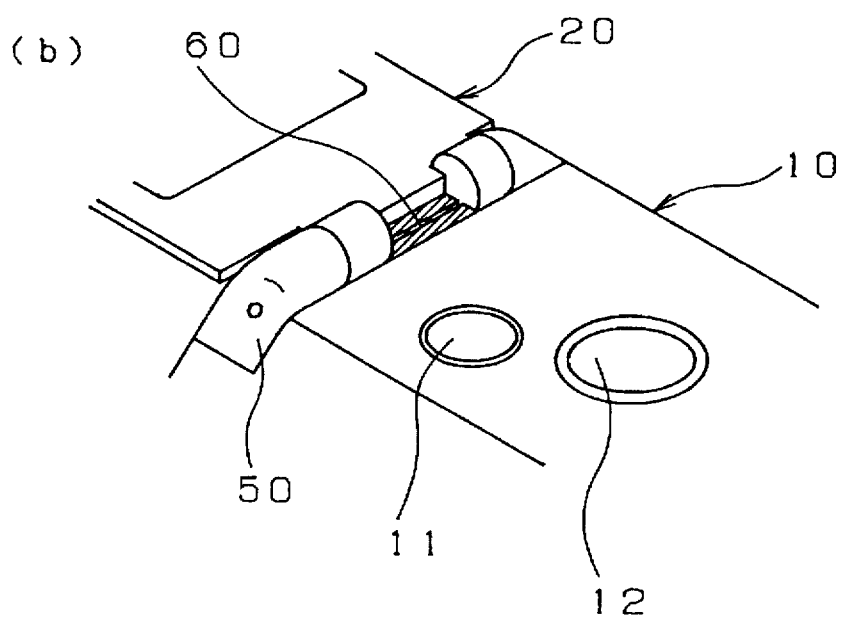

This construction of the connection unit allows the large housing 41 to be mounted on the small housing 42 after mounting the hinge piece 50 on the small housing 42 and further mounting the cover 20 on the hinge piece 50, so that wiring between the LCD 21 in the cover 20 and a printed circuit board within the main housing 40 is simplified. When wiring is made by employing a cable of a flexible printed circuit (FPC), the cable should be drawn within the main housing 40 through an inner side of a blind portion 55 of the hinge piece 50 and a cut-out portion 45 of the small housing 42. When the cover 20 is closed as shown at (a) of FIG. 7, one cannot see the cable from the external because the cable is located inside the blind portion 55. The gap between the blind portion 55 and one end of the cover 20 confronting the portion 55 is designed to be about 1 mm for a smooth open-and-close movement of the cover 20. When the cover 20 is opened as shown at (b) of FIG. 7, the cable 60 appears between cover 20 and main body 10.

Removing the cover 20 from the main body 10 to repair or replace the LCD 21 is easily performed by removing the spring pins 52 because the cover 20 is attached to the hinge piece 50, viz., the open-and-close mechanism for the cover 20 is provided by the small piece 50 separated from the main housing 40. If the cover 20 is secured to the main housing 40 by employing spring pins or the like, the assembly cannot be disassembled after assembling and the main housing 40 has to be replaced to repair or replace the LCD 21.

If desired, the cover 20 may be modified to form a single unit with the main body (main housing) by employing plastics which is easily bent or extended, or to be mounted on the main body by a hinge. Retaining the cover at a predetermined angle may be performed by utilizing frictional force or employing a locking or notching mechanism for locking the cover at the predetermined angle.

Figure 12:
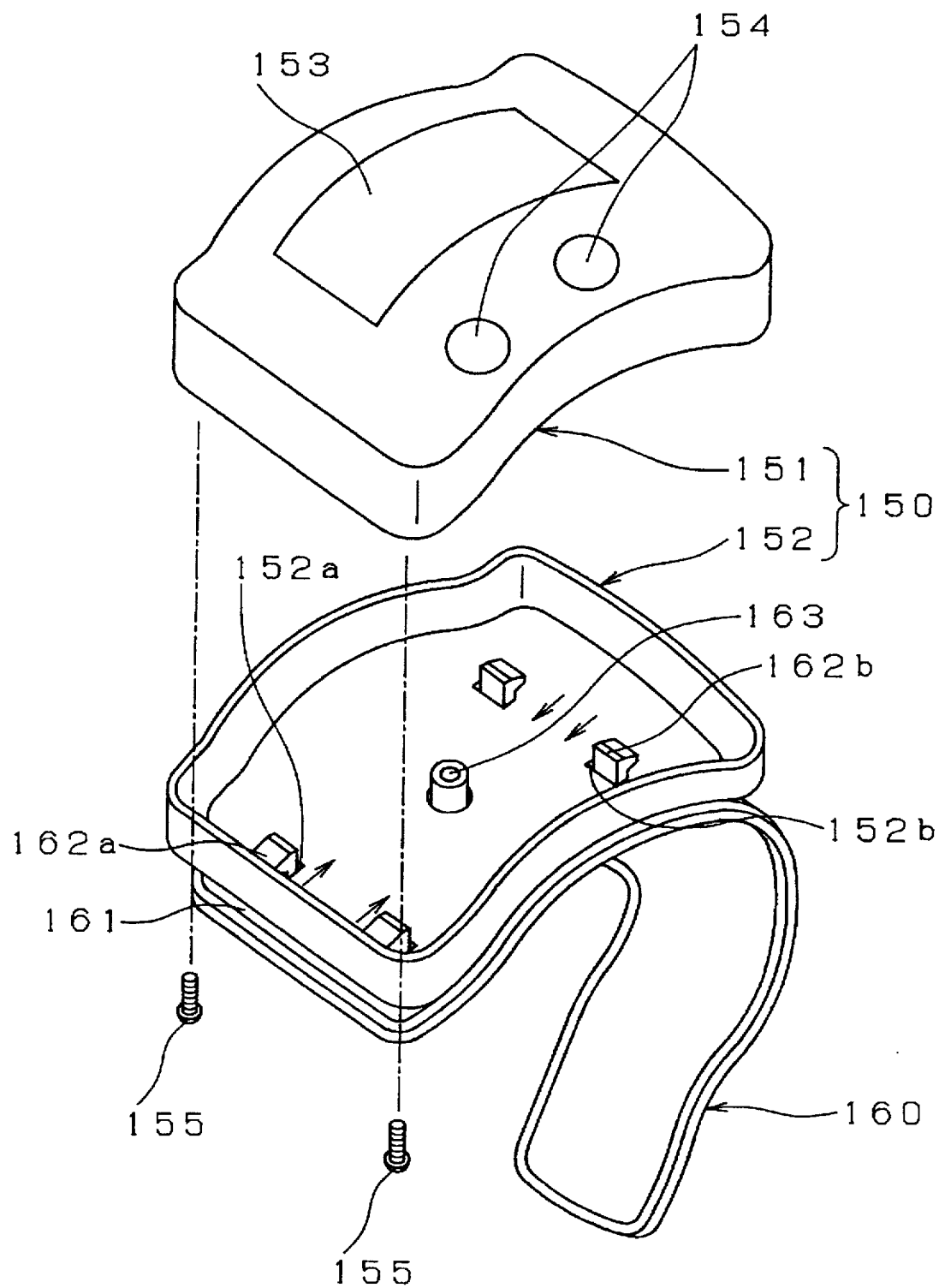
FIG. 12 is a perspective view of an attachment structure which is applicable to a blood pressure monitor of this invention.
Figure 13:
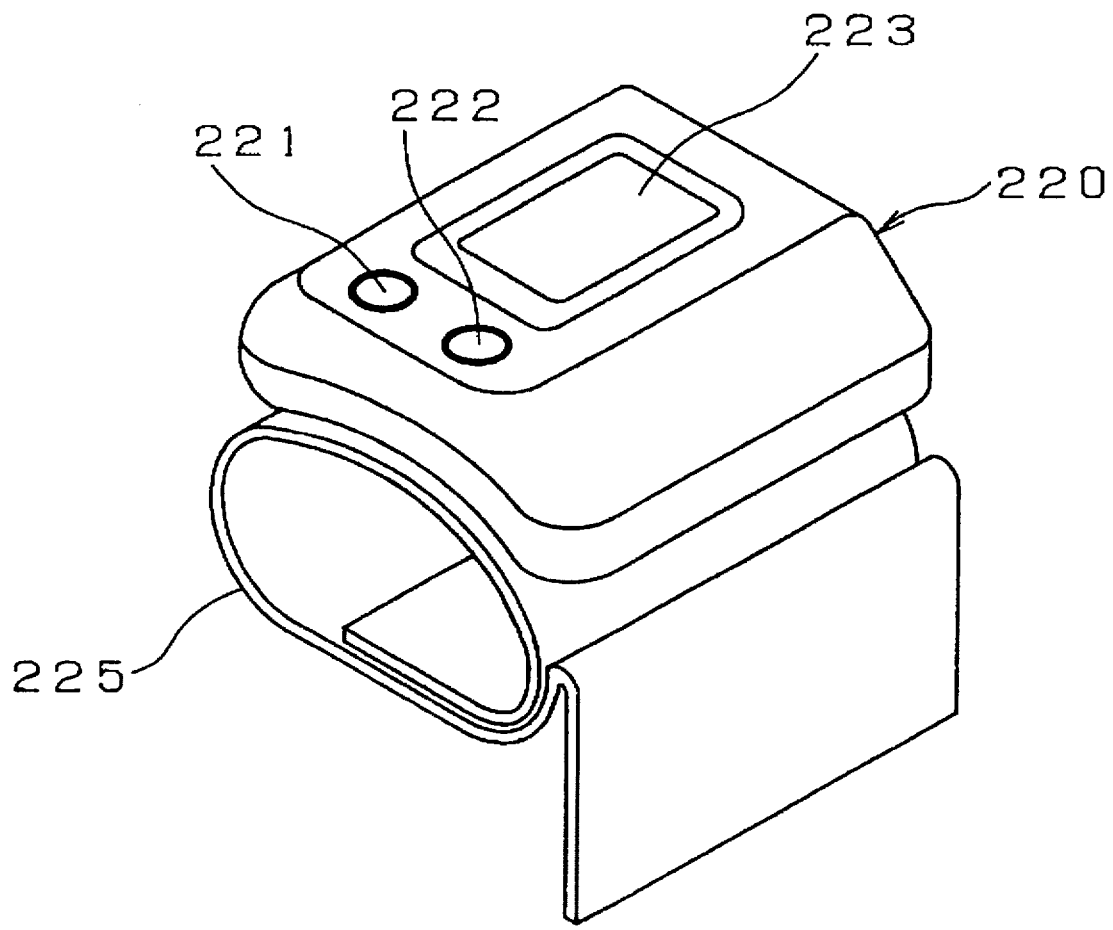
FIG. 13 is a perspective external view of a conventional blood pressure monitor.

A mechanical structure for attaching or detaching a cuff with respect to a main body of a blood pressure monitor will be described hereinafter. FIG. 12 shows a blood pressure monitor to illustrate engagement between a detachable cuff 160 and a main housing 150 consisting of an upper housing 151 and a lower housing 152, which is applicable to this invention. The main housing 150 is associated with a display 153 displaying measured data and switches 154 including a power switch. The housings 151 and 152 are coupled each other and secured by screws 155.

An attachment portion (flexible plate) 161 of the cuff 160 attached to the main housing 150 is provided with two pairs of hooks 162a and 162b which project outwardly. Corresponding to the hooks 162a and 162b, there are provided two pairs of openings 152a and 152b on the lower housing 152. An air inlet-and-outlet tube 163 disposed on the cuff 160 pierces the lower housing 152. The hooks 162a and 162b on the cuff 160 are fitted to the openings 152a and 152b on the lower housing 152 for engagement to thereby secure the cuff 160 to the housing 150 as a single unit. To avoid unexpected detachment of the cuff 160 from the main housing 150, the hooks and the openings are firmly engaged one another. In order to detach the cuff 160 from the main housing 150 to repair, replace or inspect a pressure sensor, initially the screws 155 are removed, the upper housing 151 is removed from the lower housing 152 to open the main housing 150, and the hooks 162a and 162b are pushed inwardly as shown by arrow marks of FIG. 12 to be released from the openings 152a and 152b. Thus, in this attachment structure between the cuff 160 and the main housing 150, attachment of the cuff to the main housing is easy, but detachment of the cuff is rather complicated.

Figure 8:
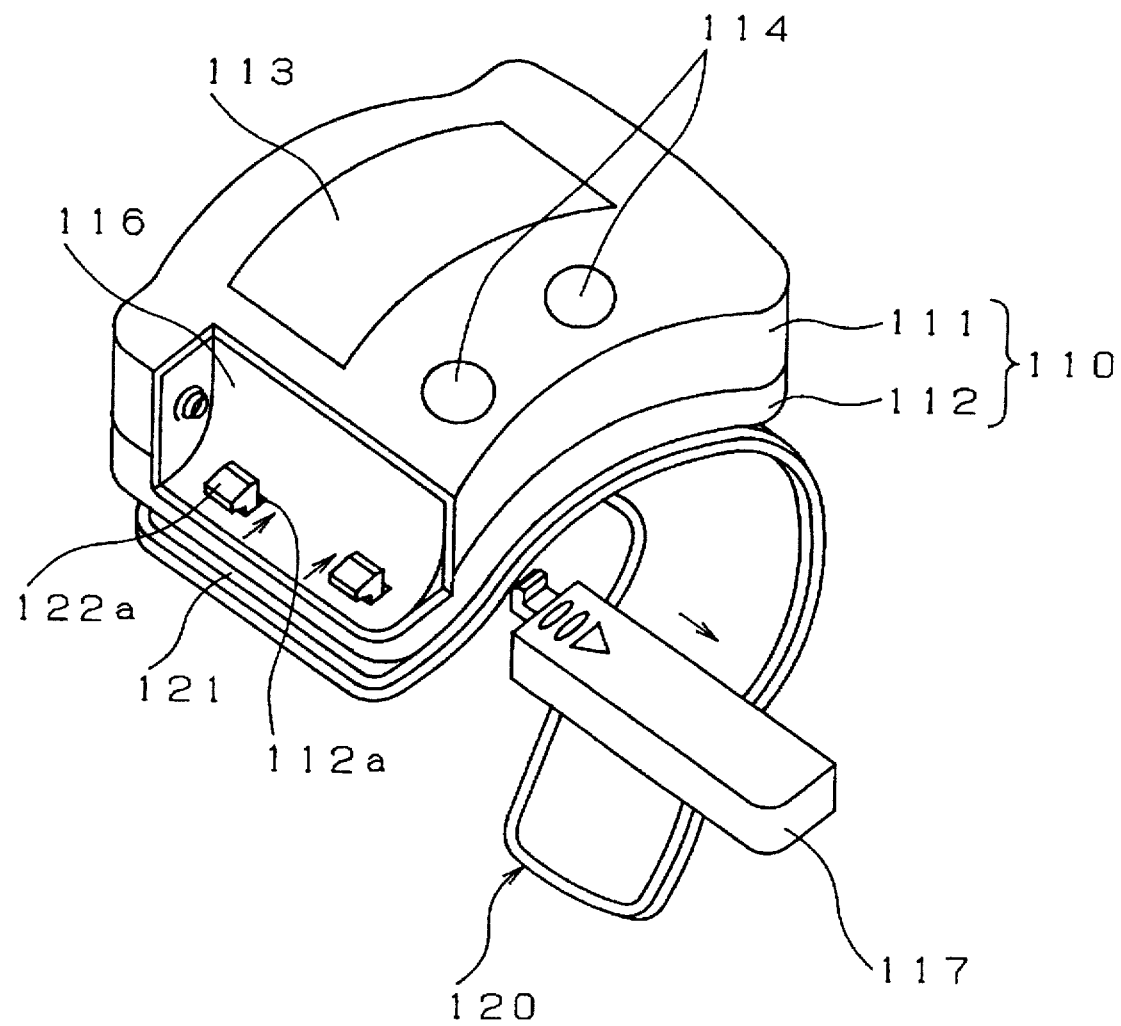
FIG. 8 is a perspective view of a blood pressure monitor to show an attachment structure for a main body and a cuff as a further embodiment of this invention.
Figure 9:
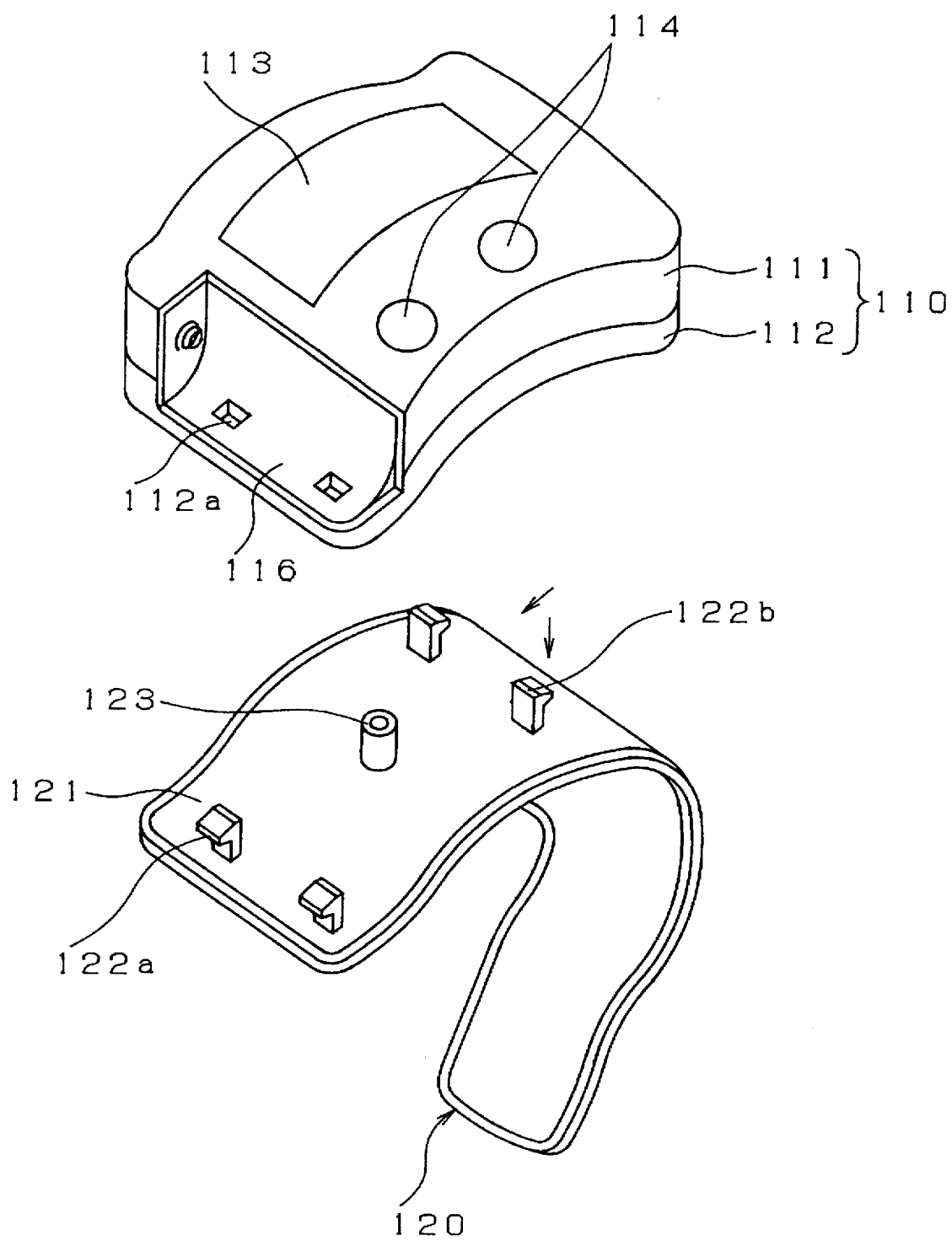
FIG. 9 is a perspective view of the monitor of FIG. 8 in which the cuff is detached from the main body.

FIGS. 8 and 9 show an improved attachment structure between a cuff 120 and a main housing 110 for easy detachment of the cuff as a further embodiment of this invention. It should be understood that a display 113 is shown to be disposed on a main housing 110 in a blood pressure monitor of FIG. 8, but the monitor may be modified to employ a cover carrying the display to be mounted on the main housing as described in the foregoing embodiments.

The blood pressure monitor of FIG. 8 includes main housing 110 associated with display 113 showing measured data and switches 114 including a power switch, and cuff 120 detachably mounted on the main housing. The main housing 110 consists of an upper housing 111 and a lower housing 112 which are coupled together and secured by screws (not shown in drawings) in the same manner as shown in FIG. 12. A battery storage compartment 116 is disposed on one end of the main housing 110, and a battery lid 117 is adapted to be removably mounted over the chamber 116.

As shown in FIGS. 8 and 9, a mounting portion 121 (flexible plate) of the cuff 120 is provided with a pair of hooks 122a at one end of the cuff and a pair of hooks 122b in inner position which respectively project outwardly along the cuff. On the mounting portion 121 there is disposed an air inlet-and-outlet tube 123. A pair of openings 112a for engagement with the pair of hooks 122a are disposed in the battery storage chamber 116 of the main housing 110, a pair of openings (not shown in drawings) engaged with the pair of hooks 122b are disposed on the lower housing 112. The strength of engagement between the hooks and the openings is so designed that the cuff is not easily detached from the main housing 110 even if the cuff is tried to be pulled outwardly. The hooks 122a exposed within the battery chamber 116 are designed to not interrupt storage of a battery.

In thus constructed blood pressure monitor, attaching the cuff 120 to the main housing 110 is performed by inserting the hooks 122a and 122b of the cuff into the corresponding openings (112a) for engagement as performed in the monitor of FIG. 12. In order to detach the cuff 120 from the main housing 110, initially the lid 117 is removed from the main housing 110 to open the chamber 116, the hooks 122a exposed within the chamber are inwardly depressed (in an arrow marked direction) to be pulled out from the openings 112a, the cuff 120 is shifted toward the battery chamber 116 to pull out the hooks 122b from the corresponding openings. Accordingly, the cuff can be removed from the main housing without opening the main housing 110, whereby attachment and detachment of the cuff 120 is simplified.

Figure 10:
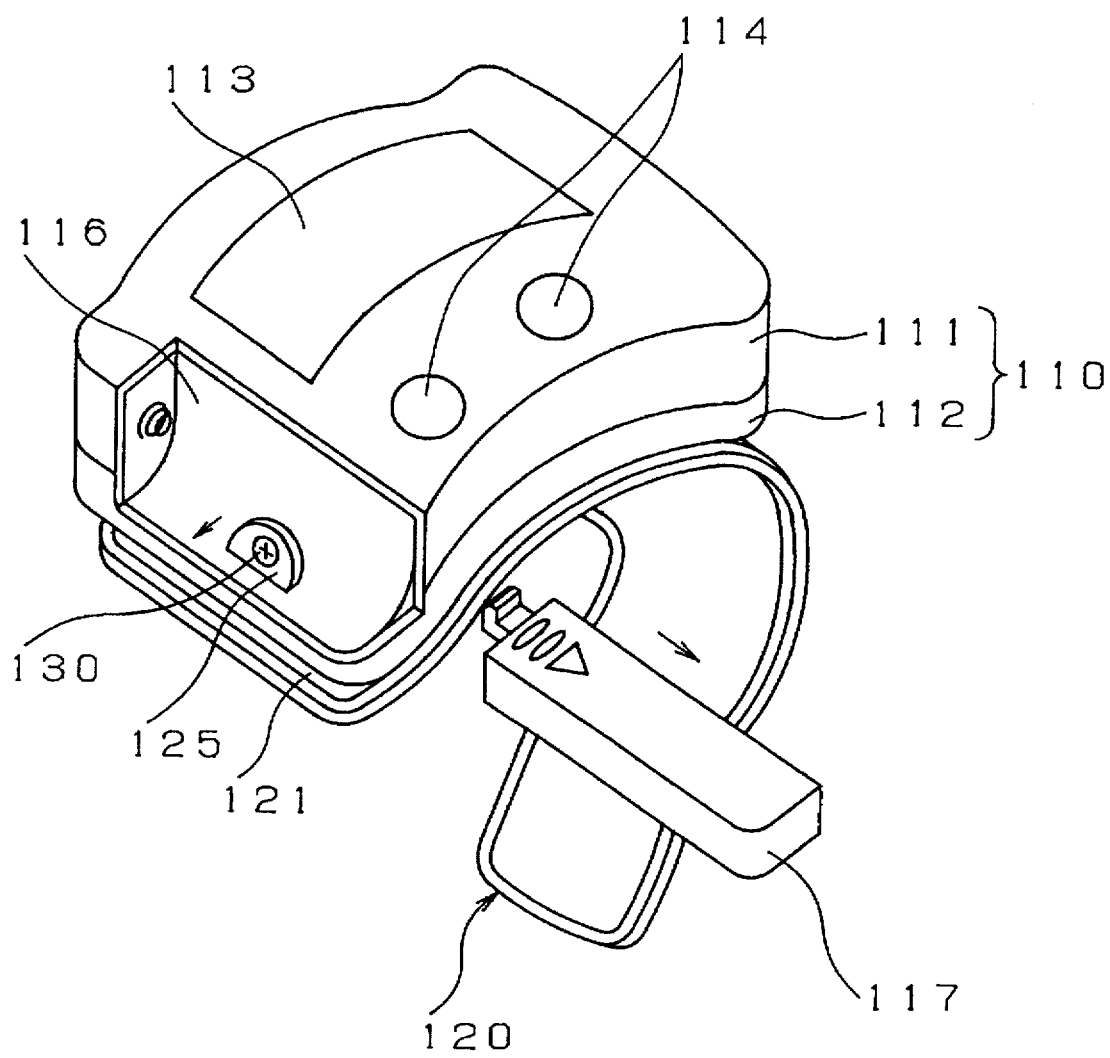
FIG. 10 is a perspective view of a blood pressure monitor employing a modified attachment structure for a main body and a cuff as a modification of the monitor of FIG. 8.
Figure 11:
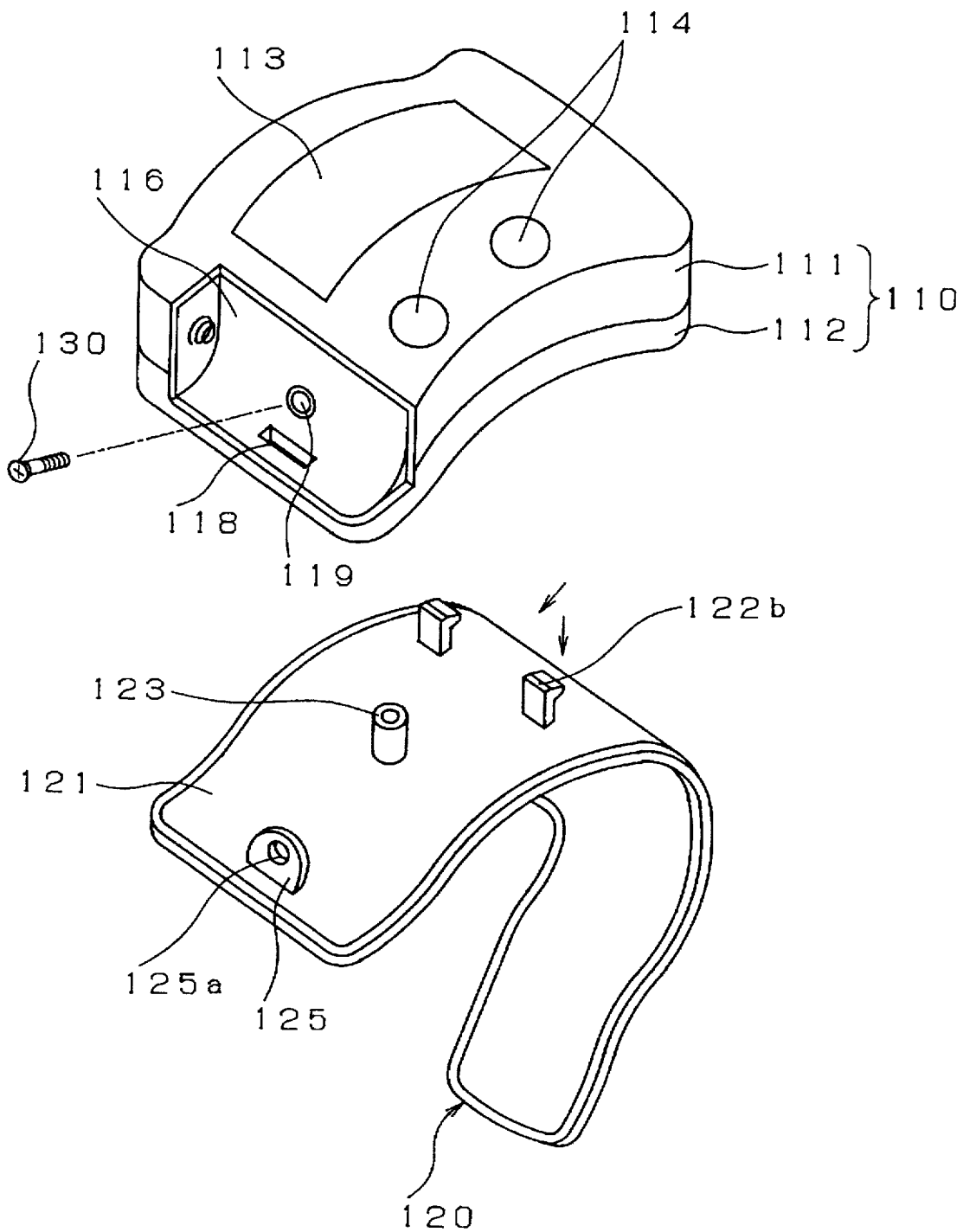
FIG. 11 is a perspective view of the monitor of FIG. 10 in which the cuff is detached from the main body.

In FIGS. 10 and 11 there is shown a blood pressure monitor as a modification of the blood pressure monitor of FIG. 8. The same components as those of the blood pressure monitor of FIG. 8 are represented by the same reference numerals. On one end of flexible plate 121 of cuff 120 there is disposed a projection 125 provided with a screw hole 125a. In the battery chamber 116 there are disposed an opening 118 for accommodating the projection 125 and a threaded (tapped) hole 119 for securing the projection 125 to the main housing 110 by a screw 130. Other construction is the same as that of the monitor of FIG. 8.

The cuff 120 is attached to the main housing 110 by inserting the pair of hooks 122b into the corresponding openings (not shown in drawings) of the main housing 110 for engagement, piercing the projection 125 through the opening 118, and securing the projection 125 to the housing 110 in a fixed position by the screw 130. Detaching the cuff is performed by a reversal operation. The cuff is detached by removing the lid 117 from the housing 110, unscrewing the screw 130 to remove the projection 125 from the opening 118, shifting the cuff toward the battery chamber 116 to pull out the hooks 112b from the corresponding openings. Thus, the cuff 120 may be easily attached to or detached from the main housing 110 without opening the housing.

This invention is not limited to the foregoing embodiments. Though a pair of hooks 122a are employed in the blood pressure monitor of FIG. 8, only one hook 122a may be employed, so that three hooks are employed in total and only one opening 112a is employed within the battery storage chamber 116. Though in FIG. 9 the hooks 122a and 122b are disposed outwardly along the cuff, they may be arranged inwardly, in which the cuff is detached from the housing by pushing the hooks outwardly and shifting the cuff in a direction opposite to the battery chamber. If desired, the battery storage chamber may be disposed on an opposite end of the main housing 110.

While the invention has been described and illustrated with respect to certain embodiments which give satisfactory results, it will be understood by those skilled in the art, after understanding the purpose of the invention, that various other changes and modifications may be made without departing from the spirit and scope of the invention, and it is therefore, intended in the appended claims to cover all such changes and modifications.

What is claimed is:

1. A blood pressure monitor comprising:

a main body;

an operation switch disposed on an upper wall of the main body;

a cuff attached to a lower wall of the main body;

a cover mounted on the main body in an open-and-close fashion;

a display disposed on a wall of the cover confronting the operation switch for displaying measured data, the operation switch being covered by the cover when the cover is closed; and in which one end of the cover is so mounted on a shaft disposed on one end of the main body, that the cover is pivotable, wherein the shaft is inclined with respect to an opposite end of said main body to one end thereof and an opposite end of said cover to said one end thereof so that said main body and said cover make a predetermined angle of inclination.

2. A blood pressure monitor comprising:

a main body;

an operation switch disposed on an upper wall of the main body;

a cuff attached to a lower wall of the main body;

a cover mounted on the main body in an open-and-close fashion;

a display disposed on a wall of the cover confronting the operation switch for displaying measured data, the operation switch being covered by the cover when the cover is closed; and in which one end of the cover is so mounted on a shaft disposed on one end of the main body, that the cover is pivotable, wherein the shaft has a conical configuration to provide a predetermined angle of inclination by said main body and said cover.

3. The blood pressure monitor according to claim 1 or 2, wherein said predetermined angle of inclination is between 20 degrees and 30 degrees.

4. A blood pressure monitor comprising a main housing, a cuff attached to a lower wall of said main housing, a battery storage chamber disposed within said main housing, attaching means within said battery storage chamber for attaching said cuff to said main housing.

5. A blood pressure monitor according to claim 4, in which said attaching means is an opening to be engaged by a hook disposed on said cuff.

6. A blood pressure monitor according to claim 4, in which said attaching means includes an opening to be pierced by a projection disposed on said cuff and a screw for securing said projection piercing through said opening to a wall of said battery storage chamber.

\* \* \* \* \*

(12) EX PARTE REEXAMINATION CERTIFICATE (7748th)
United States Patent
Inagaki et al.

(10) Number: US 5,687,732 C1
(45) Certificate Issued: Sep. 21, 2010

(54) BLOOD PRESSURE MONITOR

(75) Inventors: Takashi Inagaki, Kyoto (JP); Toshiyuki Kobayashi, Kyoto (JP)

(73) Assignee: Omron Healthcare Co., Ltd., Ukyou-Ku, Kyoto--Shi, Kyoto (JP)

Reexamination Request:
No. 90/006,139, Nov. 7, 2001

Reexamination Certificate for:
Patent No.: 5,687,732
Issued: Nov. 18, 1997
Appl. No.: 08/539,911
Filed: Oct. 6, 1995

(30) Foreign Application Priority Data

Oct. 7, 1994 (JP) ............................................. 6-243926
Jan. 18, 1995 (JP) ............................................. 7-005716

(51) Int. Cl.
G04B 37/00 (2006.01)
G04B 37/14 (2006.01)
A61B 5/022 (2006.01)

(52) U.S. Cl. ...................... 600/485; 600/490; 600/503; D14/344

(58) Field of Classification Search .................. None
See application file for complete search history.

(56) References Cited

U.S. PATENT DOCUMENTS 4,998,534 A  3/1991  Claxton et al. ............... 128/670
5,201,319 A  4/1993  Negishi ...................... 128/672

FOREIGN PATENT DOCUMENTS

| JP | 56-5639 A | 1/1981 |
|---|---|---|
| JP | 59-112170 U | 1/1983 |
| JP | 61-133006 U | 8/1985 |
| JP | 61-191008 U | 11/1985 |
| JP | 60-249938 A | 12/1985 |
| JP | 1-265939 A | 10/1989 |
| JP | 2-82305 U | 6/1990 |
| JP | 3-221030 A | 9/1990 |
| JP | 7-143970 A | 6/1995 |

*Primary Examiner*—Robert L Nasser

(57) ABSTRACT

A blood pressure monitor includes a main body provided with a power switch and an inflating switch, a cover mounted on the main body in an open-and-close fashion and on an inner wall thereof provided with a display, and a cuff secured to the main body as a single unit. When the cover is closed during not using the monitor, the power and inflating switches are covered with the cover. When the cover is opened for use, the display appears. Thus, the blood pressure monitor provides avoidance of unexpected actuation of the power and inflating switches, improvement of operation of the switches and a view angle of the display, improved assembling work of the monitor, and simplification of repair and replacement in the monitor.

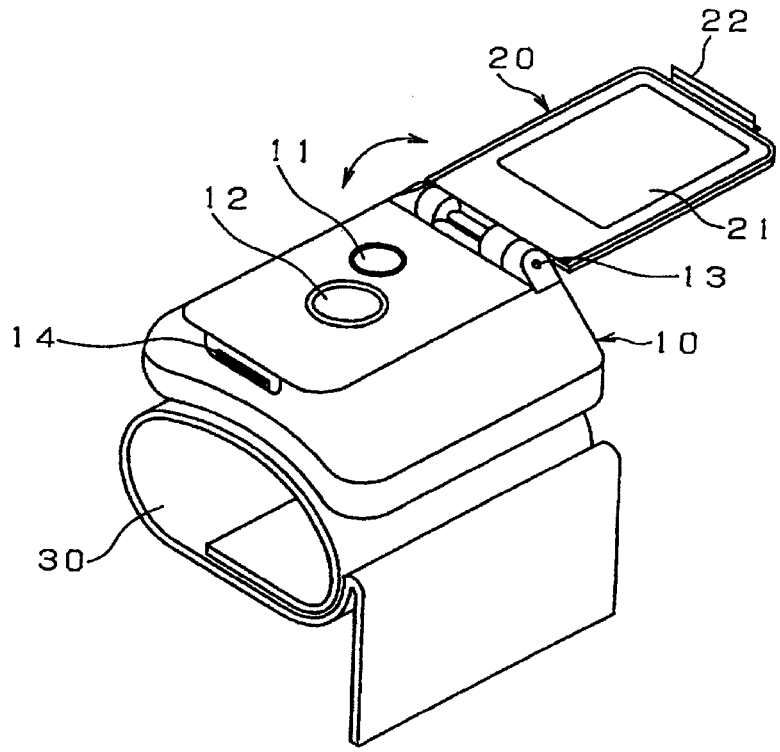

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-3 is confirmed.

Claims 4-6 are cancelled.

New claims 7-12 are added and determined to be patentable.

*7. A blood pressure monitor, comprising:*
*a main housing having a longitudinal axis;*
*a cuff including first attaching means and first hooks for attaching the cuff to a lower wall of the main housing;*
*a battery storage chamber disposed within the main housing and including second attaching means within the battery storage chamber and cooperating with the first attaching means; and*
*first openings provided in the main housing outside the battery storage chamber and cooperating with the first hooks,*
*wherein the first hooks are configured to be releasable from the first openings by shifting the cuff in a direction of the longitudinal axis toward or away from the battery storage chamber after releasing the first attaching means from the second attaching means, and*
*wherein the cuff includes no hook that is both aligned orthogonally to any of the first hooks and configured to cooperate with an opening in the main housing outside the battery storage chamber.*

*8. The blood pressure monitor according to claim 7; wherein the first attaching means comprises second hooks and the second attaching means comprises second openings engaged by the second hooks.*

*9. The blood pressure monitor according to claim 7, wherein the first attaching means includes a projection and the second attaching means includes an opening configured to be pierced by the projection, and a screw for securing the projection piercing through the opening to a wall of the battery storage chamber.*

*10. A blood pressure monitor, comprising:*
*a main housing having a longitudinal axis;*
*a cuff including first attaching means and at least one first hook for attaching the cuff to a lower wall of the main housing;*
*a battery storage chamber disposed within the main housing and including second attaching means within the battery storage chamber and cooperating with the first attaching means; and*
*at least one first opening provided in the main housing outside the battery storage chamber and cooperating with the at least one first hook,*
*wherein the at least one first hook is configured to be releasable from the at least one first opening by shifting the cuff in a direction of the longitudinal axis toward or away from the battery storage chamber after releasing the first attaching means from the second attaching means, and*
*wherein the cuff includes no hook that is both aligned orthogonally to any of the at least one first hooks and configured to cooperate with an opening in the main housing outside the battery storage chamber.*

*11. The blood pressure monitor according to claim 10, wherein the first attaching means comprises at least one second hook and the second attaching means comprises at least one second opening engaged by the at least one second hook.*

*12. A blood pressure monitor, comprising:*
*a main housing having a longitudinal axis;*
*a cuff including first attaching means and at least one first hook for attaching the cuff to a lower wall of the main housing;*
*a battery storage chamber disposed within the main housing and including second attaching means within the battery storage chamber and cooperating with the first attaching means; and*
*at least one first opening provided in the main housing outside the battery storage chamber and cooperating with the at least one first hook,*
*wherein the at least one first hook is configured to be releasable from the at least one first opening by shifting the cuff in a direction of the longitudinal axis toward or away from the battery storage chamber after releasing the first attaching means from the second attaching means and*
*wherein the first attaching means includes a projection and the second attaching means includes an opening configured to be pierced by the projection, and a screw for securing the projection piercing through the opening to a wall of the battery storage chamber.*

\* \* \* \* \*